United States Patent [19]

Minter

[11] Patent Number: 5,910,406

[45] Date of Patent: Jun. 8, 1999

[54] MANIPULATING NUCLEIC ACID SEQUENCES

[75] Inventor: Stephen Minter, New Mills, United Kingdom

[73] Assignee: Tepnel Medical Limited, United Kingdom

[21] Appl. No.: 08/256,132

[22] PCT Filed: Dec. 23, 1992

[86] PCT No.: PCT/GB92/02394

§ 371 Date: Aug. 5, 1994

§ 102(e) Date: Aug. 5, 1994

[87] PCT Pub. No.: WO93/13220

PCT Pub. Date: Jul. 8, 1993

[30] Foreign Application Priority Data

Dec. 24, 1991 [GB] United Kingdom .................. 9127415

[51] Int. Cl.$^6$ ............................. C12Q 1/68; C07H 21/02; C08G 63/48; B32B 5/16
[52] U.S. Cl. ........................... 435/6; 536/23.1; 536/24.3; 525/54.11; 428/403
[58] Field of Search .............................. 435/6; 525/54.11; 536/23.1, 24.3; 428/403

[56] References Cited

U.S. PATENT DOCUMENTS

| | | | |
|---|---|---|---|
| 4,746,572 | 5/1988 | Glajch et al. | 428/403 |
| 4,824,776 | 4/1989 | Heller | 435/6 |
| 5,427,930 | 6/1995 | Birkenmeyer et al. | 435/91.52 |
| 5,629,158 | 5/1997 | Uhlen et al. | 435/6 |

FOREIGN PATENT DOCUMENTS

| | | |
|---|---|---|
| 0184056 | 6/1986 | European Pat. Off. . |
| 0 200 113 | 11/1986 | European Pat. Off. . |
| 297379 | 1/1989 | European Pat. Off. . |
| 0 457 343 | 11/1991 | European Pat. Off. . |
| WO86/05815 | 10/1986 | WIPO . |
| 8607281 | 12/1986 | WIPO . |
| 8909282 | 10/1989 | WIPO . |
| WO89/11546 | 11/1989 | WIPO . |

(List continued on next page.)

OTHER PUBLICATIONS

Oliver, Stephen G., et al. "A Dictionary of Genetic Engineering", Cambridge University Press, 1985, pp. 31.

Hultman et al., Biotechniques 10(1):84–93 (1991).

Hultman et al., Nucleic Acids Research 17(13) : 4937–4945 (1989).

Horvath et al. Methods in Enzymology 154: 314–326 (1987).

*Primary Examiner*—W. Gary Jones
*Assistant Examiner*—Ethan Whisenant
*Attorney, Agent, or Firm*—Akin, Gump, Strauss, Hauer & Feld

[57] ABSTRACT

A method of effecting a manipulation of a nucleic acid sequence comprises (a) providing a solid support system having bonded thereto a single stranded oligonucleotide complementary to a specific sequence on a target nucleic acid longer than said oligonucleotide, (b) adding a source of single stranded target nucleic acid to the solid support system, (c) hybridising the target nucleic acid to the oligonucleotide, and (d) effecting the manipulation on the hybridised target nucleic acid. The manipulation may for example be a copying or amplification of the target nucleic acid sequence. In a preferred embodiment, the support is provided in a flow-through vessel which facilitates washing of the support to remove impurities and leave a "clean" sample of target nucleic acid on which the manipulation may be carried out. The support preferably has a siloxane matrix to which the oligonucleotide is bound. This provides a stable linkage between the oligonucleotide and the support. The method is particularly useful for analysis of medical samples.

40 Claims, 11 Drawing Sheets

FOREIGN PATENT DOCUMENTS

| | | |
|---|---|---|
| 9006042 | 6/1990 | WIPO . |
| 9009455 | 8/1990 | WIPO . |
| WO90/11369 | 10/1990 | WIPO . |
| WO92/08808 | 5/1992 | WIPO . |
| 9303052 | 2/1993 | WIPO . |
| 9304199 | 3/1993 | WIPO . |
| WO93/04199 | 3/1993 | WIPO . |
| 9309250 | 5/1993 | WIPO . |
| WO93/09250 | 5/1993 | WIPO . |
| 9315228 | 8/1993 | WIPO . |
| WO93/15221 | 8/1993 | WIPO . |
| 9409156 | 4/1994 | WIPO . |

MANIPULATING NUCLEIC ACID SEQUENCES

The present invention relates to a method and apparatus for carrying out manipulations on nucleic acid sequences using a solid support system, as well as to supports for use in the method and apparatus.

Various procedures are known for manipulating nucleic acid sequences. For example, EP-A-0 200 362 (Cetus) describes a liquid phase process for amplifying, detecting and/or cloning nucleic acid sequences. The process comprises the following steps (i) treating separate complementary strands of the nucleic acid sequence with two oligonucleotide primers each of which hybridises to one of the strands;

(ii) extending the primers to form double stranded nucleic acid sequences;

(iii) denaturing the product from (ii) to produce single strands of nucleic acid; and (iv) using the single strands from (iii) in a repeat of steps (i)–(iii) the overall procedure being repeated as often as necessary.

It is a feature of this prior technique that both complementary strands are used as templates for the second and further amplification steps. Furthermore in the method of EP-A-0 200 362 the reactant mixture includes unhybridised target nucleic acid, unhybridised copy target, and unhybridised primer which makes the system very inefficient. Additionally any mistake which occurs in the copying at any stage results in the mistake being copied into the "chain reaction".

Amplification techniques using solid phase support systems are also known, for example DYNAL (Trade Mark) magnetic beads as disclosed in EP-A-0 091 453 and EP-A-0 106 873. In use of such beads, DNA is synthesised onto a magnetic bead and then cleaved therefrom by ammonium hydroxide. The beads may then be separated from the synthesised DNA using a magnet. Alternatively, biotin may be added to one end of a synthesised or natural DNA sequence and the sequence recovered using a magnetic bead which has been pre-conjugated to streptavidin (thereby attracting the biotin to recover the DNA). A problem with this type of solid support is that the biotin streptavidin linkage is biodegradable.

Other known solid support systems include porous silicas. The presence of the pores can create problems since nucleotide chain growth occurs within the pores, resulting in inefficient washing and residues remaining within the pores, again reducing the yield and resulting in relatively inefficient coupling.

Ep-A-0 184 056 describes a method for the large scale production of DNA probes using a solid substrate. The process of this prior specification comprises covalently linking to a solid substrate a polynucleotide complementary to the probe to be produced and then hybridising the polynucleotide with an oligonucleotide which acts as a primer. The oligonucleotide is then extended in a direction away from the substrate (using the polynucleotide as a template) thereby to produce an extended sequence complementary to the bound polynucleotide. The hybridised polynucleotide and extended oligonucleotide are then denatured so as to release the extended oligonucleotide from the solid substrate for collection. The extended oligonucleotide may be used as an analytical probe. Thus, for example, the polynucleotide originally bound to the support may be a gene, and the extended oligonucleotide may be used as a probe for detecting the presence of that gene in a biological sample.

There are however a number of disadvantages associated with the method described in EP-A-0 184 056. In particular, if the polynucleotide to be bound to the support is not "pure" and contains other polynucleotides then these will also become bound to the support. As a result, the oligonucleotide may also hybridise to these other polynucleotides so that the extended oligonucleotide ultimately obtained may in fact be a mixture of products. Therefore, the method is not particularly good for producing "pure" samples of nucleic acid.

It is therefore an object of the present invention to obviate or mitigate the abovementioned disadvantages.

According to a first aspect of the present invention there is provided a method of effecting a manipulation of a nucleic acid sequence comprising (a) providing a solid support system having bonded thereto a single stranded oligonucleotide complementary to a specific sequence on a target nucleic acid longer than said oligonucleotide, (b) adding a source of single stranded target nucleic acid to the solid support system, (c) hybridising the target nucleic acid to the oligonucleotide, and (d) effecting the manipulation on the hybridised target nucleic acid.

The above method results in the target nucleic acid being selectively hybridised to the oligonucleotide on the support. Any impurities which are present in the system (e.g. as introduced in the sample containing the target nucleic acid) may be removed by washing to leave a "clean" sample of target nucleic acid on which the manipulation may be effected. Washing will be affected at a temperature at which the target nucleic acid does not melt off the oligonucleotide.

The target nucleic acid may for example be a purified or non-purified, native or synthesised nucleic acid. The target may be any DNA or RNA sequence from a viral, bacterial, animal or plant source.

The oligonucleotide bound to the support will generally comprise at least 8 nucleotides. Typically the polynucleotide to be hybridised thereto will comprise 1000–2000 bases and will be significantly longer than the oligonucleotide.

The oligonucleotide may be bonded to the support by reaction between suitable reactive groups provided on the support and the oligonucleotide. Alternatively the oligonucleotide may be synthesised in situ on the support.

The oligonucleotide may be bound to the solid support in the 3'-5' or the 5'-3' orientation.

Any protecting groups on the oligonucleotide are removed before the hybridisation step (c).

In the method of the invention, the single stranded target nucleic acid is hybridised to the oligonucleotide bound to the support. The oligonucleotide sequence will be very specific for the target to be hybridised. As a result, the hybridisation may be effected at a temperature which is very specific for hybridisation between the oligonucleotide and target. The hybridisation of the target nucleic acid to the oligonucleotide on the support will ideally be effected at a temperature just below (e.g. 1–3° C. below) the temperature ($T_m$) at which the target nucleic acid will "melt off" the oligonucleotide. As a general rule, $T_m$ may be calculated from the following guideline formula known in the art $$T_m = 2(A+T) + 3(G-C)$$

where A, T, G and C are respectively the number of adenine, thymine, guanine and cytosine residues present in the oligonucleotide bound to the support. The formula is usually applicable for sequences of up to about 30 nucleotides. After the hybridisation step, the supporting may be washed at a temperature slightly lower then $T_m$ thereby removing any unannealed target and impurities (e.g. proteins or unwanted nucleic acid sequences). Thus it is possible to add to the solid support system a mixture of polynucleotides (such as may be present in a biological sample) but only the specific polynucleotide of interest (i.e. the target) is retained on the support. Thus, after washing, manipulations of the polynucleotide may be effected on a "pure" sample thereof.

Successive manipulations may be carried out on the hybridised target nucleic acid. Alternatively an initial manipulation may be effected to produce a copy of the target bound to the support. This copy may then be used for subsequent manipulation operations.

Between each manipulation the support may be washed as necessary to remove impurities and produce may then be collected as required. After further washing of the support (if necessary) the manipulation may be repeated.

The manipulation may comprise for example copying, amplification of the target nucleic acid sequence, in vitro transcription, or purification of DNA binding proteins. The manipulation may also be fore detecting the presence of target by testing for hybridisation of a labelled primer to the target.

Manipulations on the polynucleotide sequence may be effected using procedures known in the art. For example, DNA polymerase 1, Klenow fragments thereof, thermostable polymerase or reverse transcriptase along with deoxynucleotide triphosphates and/or dideoxynucleotide triphosphates may be used as appropriate in the manipulation processes (described below). The nucleotides may if desired be labelled with, for example, $^{35}S$, $^{32}P$, chromophores, biotin, peroxidase, phosphatase or any other biological marker of choice.

The method of the invention is particularly useful for the analysis of samples (eg medical samples) to detect the presence (or otherwise) of a particular nucleic acid. If, for example, the sample is one being tested for a medical condition in which a relatively high amount of a particular nucleic acid (the target) is present then detection of the target nucleic acid may be effected as follows. After the target (if present) has been hybridised to the support and the latter washed to leave a "clean" sample of target, a labelled oligonucleotide primer which is known to be complementary to a sequence on the target is added to the support under conditions in which the primer will hybridise to the target. The label may, for example, be a radioactive label, a chromophore, or enzyme linked reactant. The support is then washed to remove unannealed primer, the washing being effected at a temperature below that at which primer hybridised to target nucleic acid is "melted off" the target. Subsequently the temperature of the support may be raised to melt off hybridised primer (either with or without target DNA). A detector may then be used to detect the presence of primer. If primer is detected then this is confirmation that the target nucleic acid was present in the sample.

If however the sample is one which is likely to contain only a relatively low amount of the target nucleic acid then repeated amplification reactions (see below) may be effected (each producing labelled copies of amplified product if the originally suspected target was present). A detection operation may then be effected to determine whether labelled amplification product has been produced. If so, this is confirmation that the originally suspected target was present. It will of course be appreciated that any desired number of amplifications may be performed so that the test may be made very sensitive in terms of being able to determine the presence of very small amounts of target in the original sample.

It is a significant feature of the invention that detection of the presence of target in the original sample may be achieved without the need to use separation of products on gels.

It is particularly preferred in accordance with the invention to provide the support in a flow-through vessel (e.g. a column) which facilitates the washing of the support as well as the subsequent manipulation as will be appreciated from the subsequent description.

The use of a flow-through vessel is an important feature and therefore according to a second aspect of the present invention there is provided a flow-through vessel having an inlet and an outlet and containing a solid support system having bonded thereto a single stranded oligonucleotide complementary to a specific sequence on a target nucleic acid.

The vessel may for example have a size of 150–250 $\mu$l.

The manipulation may be effected using an apparatus (in which the flow through vessel is located) for supplying reactant solutions to the vessel and for collecting and detecting the product of the manipulation.

According to a third aspect of the present invention there is provided apparatus for effecting a manipulation on a nucleic acid sequence comprising a flow through vessel storage means for storing solutions removed from the vessel during washing or other procedures, before the solutions are returned to the column, detector means for detecting products of nucleic acid manipulations, and control means for diverting solutions into and out of the vessel, into waste or storage areas and to the detector means.

In a preferred form of the apparatus, the outlet of the vessel may selectively communicate with (i) a reagent storage region, (ii) a manipulation product detection region, and (iii) a waste outlet. The reagent collection region allows reagent solution initially supplied to the vessel via the inlet thereof to be passed to the reagent collection region for subsequent return to the vessel where repeated manipulations on the same target nucleic acid are (or copy thereof) to be effected. Product from each manipulation operation may then be passed to the detection region for detection purposes. If desired, the apparatus may be such that product from successive manipulations is collected prior to being passed to the detector.

The apparatus will of course include a suitable valving arrangement (e.g. solenoid operated valves) to permit solutions, product etc. to be moved (preferably under gas pressure) through the apparatus.

The solid support may comprise non-porous particles having a size of 100 to 200 microns. The use of a non-porous material is particularly advantageous since it avoids certain problems associated with porous supports used in the prior art, namely nucleotide chain growth occurring within the pores resulting in inefficient washing and residues remaining within the pores, again reducing yield and resulting in relatively inefficient coupling. The support may be of calcined spherical particles of diameter 100 to 200 micron. The support may for example be non-porous silica gel.

The support may have reactive groups (e.g. epoxy groups) for use in immobilising the oligonucleotide sequence on the supports.

It is preferred that the support has a cross-linked siloxane matrix having reactive groups which may be used for providing an immobilised oligonucleotide on the support.

Such a support is also an important feature and therefore according to a fourth aspect of the present invention there is provided a solid support system for the immobilisation of nucleic acid sequence, wherein said support has a cross-linked siloxane matrix having reactive groups which may be used for providing an immobilised nucleic acid on the support.

According to a fifth aspect of the present invention there is provided a method of producing a support for the immobilsation of a nucleic acid sequence, the method comprising reacting a solid support having free hydroxyl groups with a siloxane matrix precursor which is reactive with said free hydroxyl groups and which has a group which may be used for the immobilisation of a nucleic acid sequence on the support and heating the product to form the siloxane matrix.

The use of the siloxane matrix is particularly advantageous due to its acid/base stability. This is in contrast to prior art supports incorporating a biotin streptavidin linkage which is biodegradable. The siloxane matrix allows a wide range of manipulations to be carried out without the oligonucleotide being removed from the support. For example, ammonia may be used as a reagent for deprotecting the oligonucleotide which remains on the support. Normal succinic acid linkages as used for immobilising oligonucleotide are base labile, causing the oligonucleotide to leave the support.

Preferably the reactive group which may be used for the immobilisation of the nucleic acid sequence is an epoxy group.

If desired, free hydroxyl groups present on the support after reaction with the siloxane matrix precursor but before formation of the cross-linked siloxane matrix may be capped e.g. by using a chlorosilane.

Preferably the siloxane matrix precursor is a glycidoxy compound of the formula

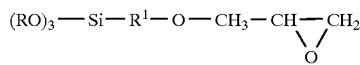

where R is an alkyl group of 1 to 4 carbon atoms and R' is an alkylene residue. Most preferably R is methyl and R' is —(CH$_2$)$_3$—.

A synthetic oligonucleotide may be covalently bound to the support via the epoxy group. Alternatively, a sodium salt of a nucleotide may be bound covalently to the support and oligonucleotide synthesis (using β-cyanoethyl phosphoamidite) may be conducted.

The invention will be further described by way of example only with reference to the accompanying drawings in which:

FIG. 1 diagrammatically represents the principle of the invention;

Figure 4A:
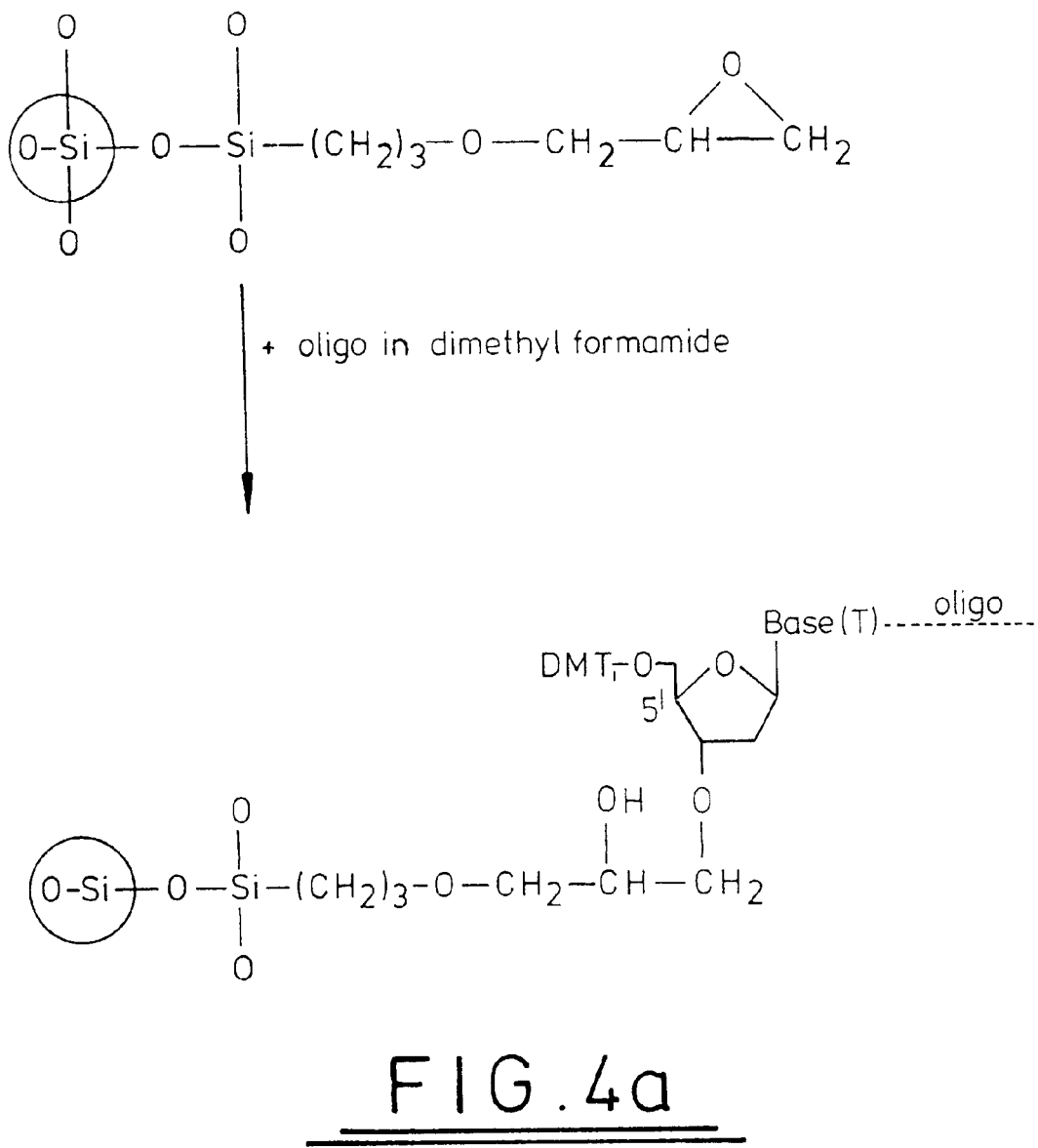
Figure 6:
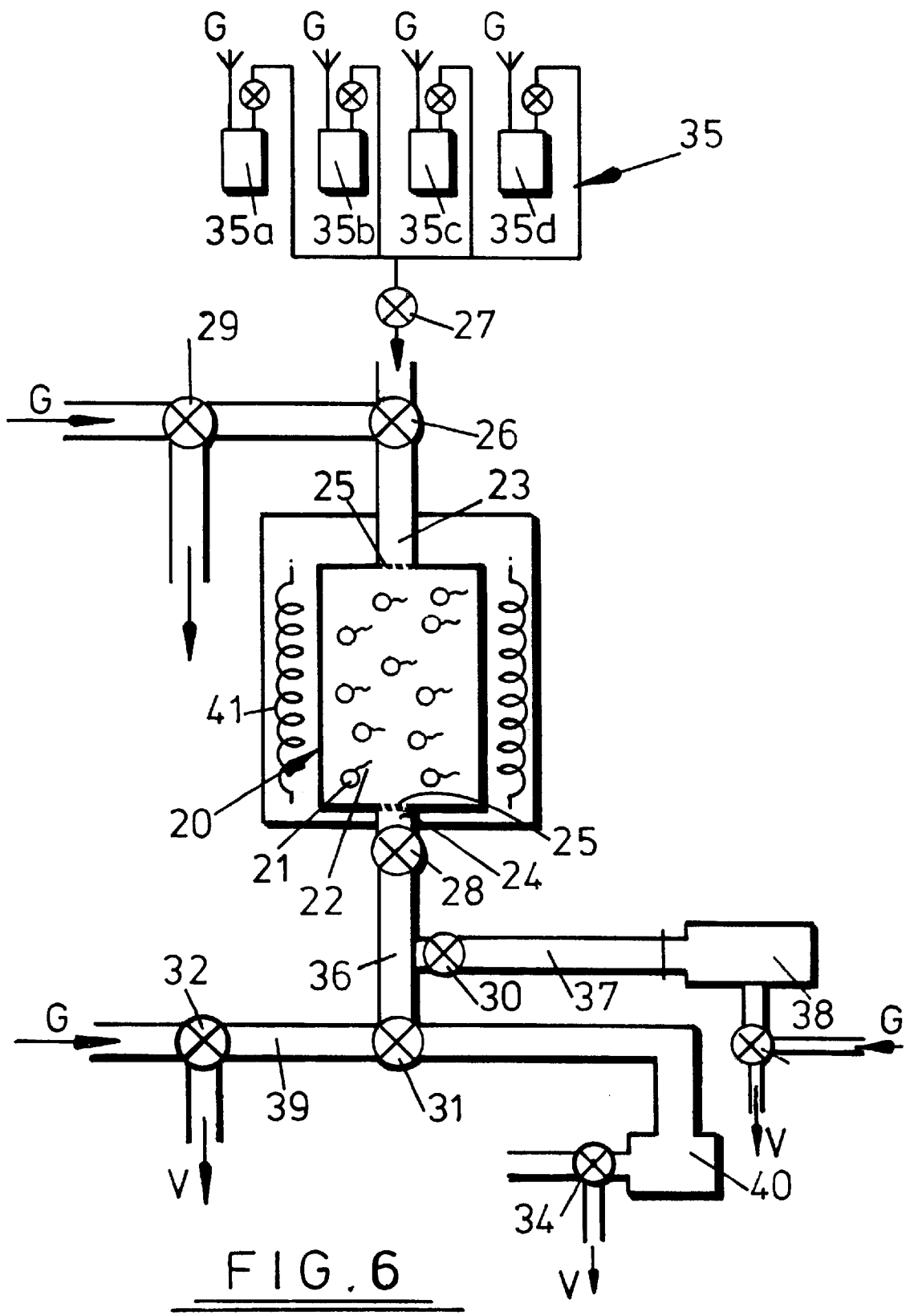
Figure 7:
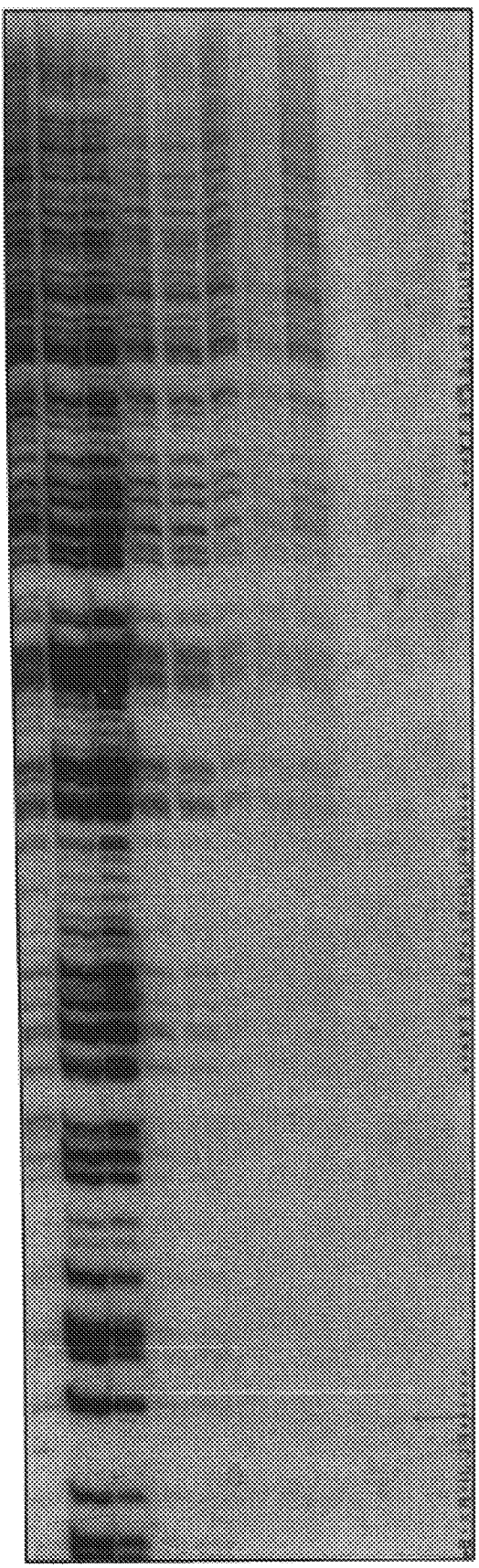

FIGS. 4a and b show a diagrammatic representation of the solid support system and reactions involved in binding an oligonucleotide thereto;

FIGS. 5a–5d shows diagrammatic representations of the steps involved in amplification of a target nucleic acid;

FIG. 6 illustrates an apparatus for effecting a manipulation in accordance with the invention; and FIG. 7 is an autoradiograph showing the results of Example 3.

Figure 1:
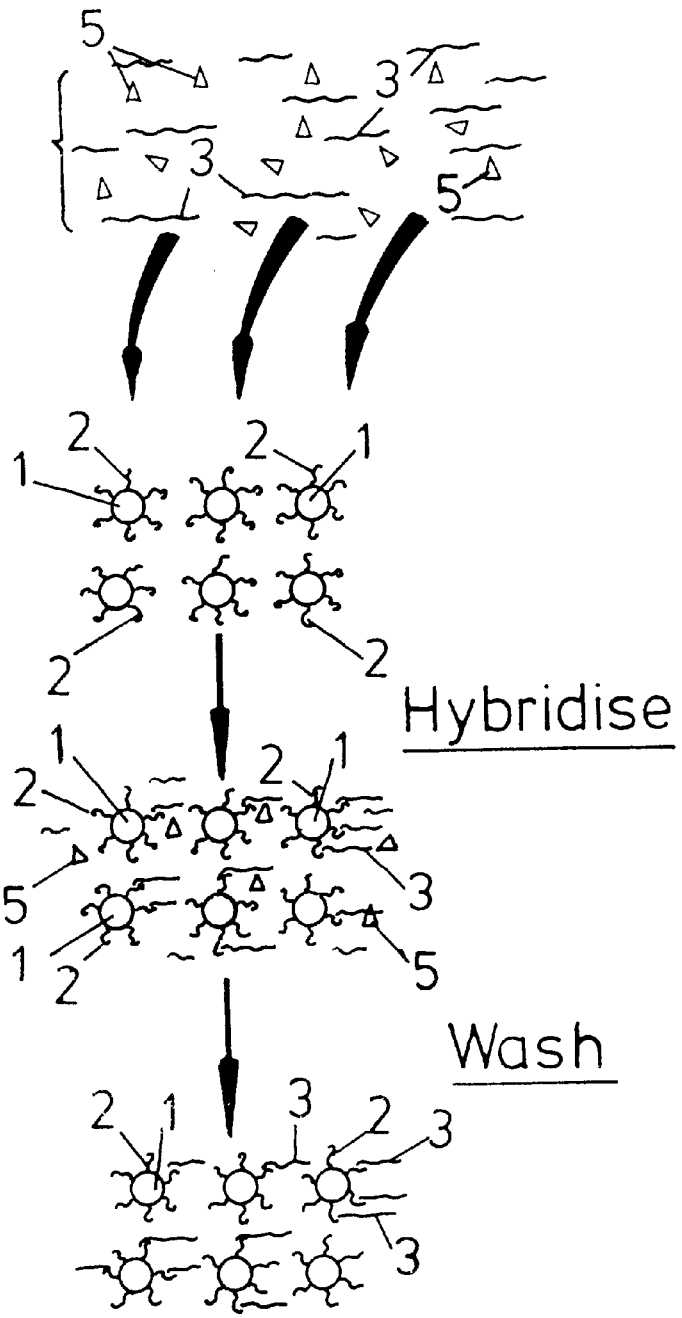
Figure 1:
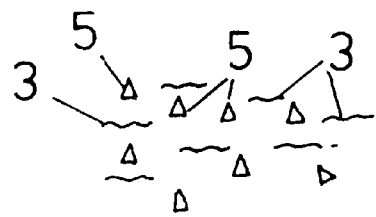

Referring to FIG. 1, there are illustrated (to a much enlarged scale) a plurality of particles 1 of a solid support material each having immobilised thereon a number of identical oligonucleotide sequences 2 which are specific for a single stranded target nucleic acid sequence 3 contained within a sample 4 which also includes unwanted impurities (e.g. other nucleic acid sequences, proteins etc.) as represented by the triangles 5.

Sample 4 is added to the support 1 under hybridising conditions such that some of the nucleic acid sequences 3 bind to the oligonucleotide leaving non-hybridised acid 3 together with the impurities 5 in the liquid phase. During subsequent washing, the non-hybridised acid 3 together with impurities 5 are removed from the support 1 as shown to leave a clean sample of target nucleic acid 3 bound to the support.

Figure 2:
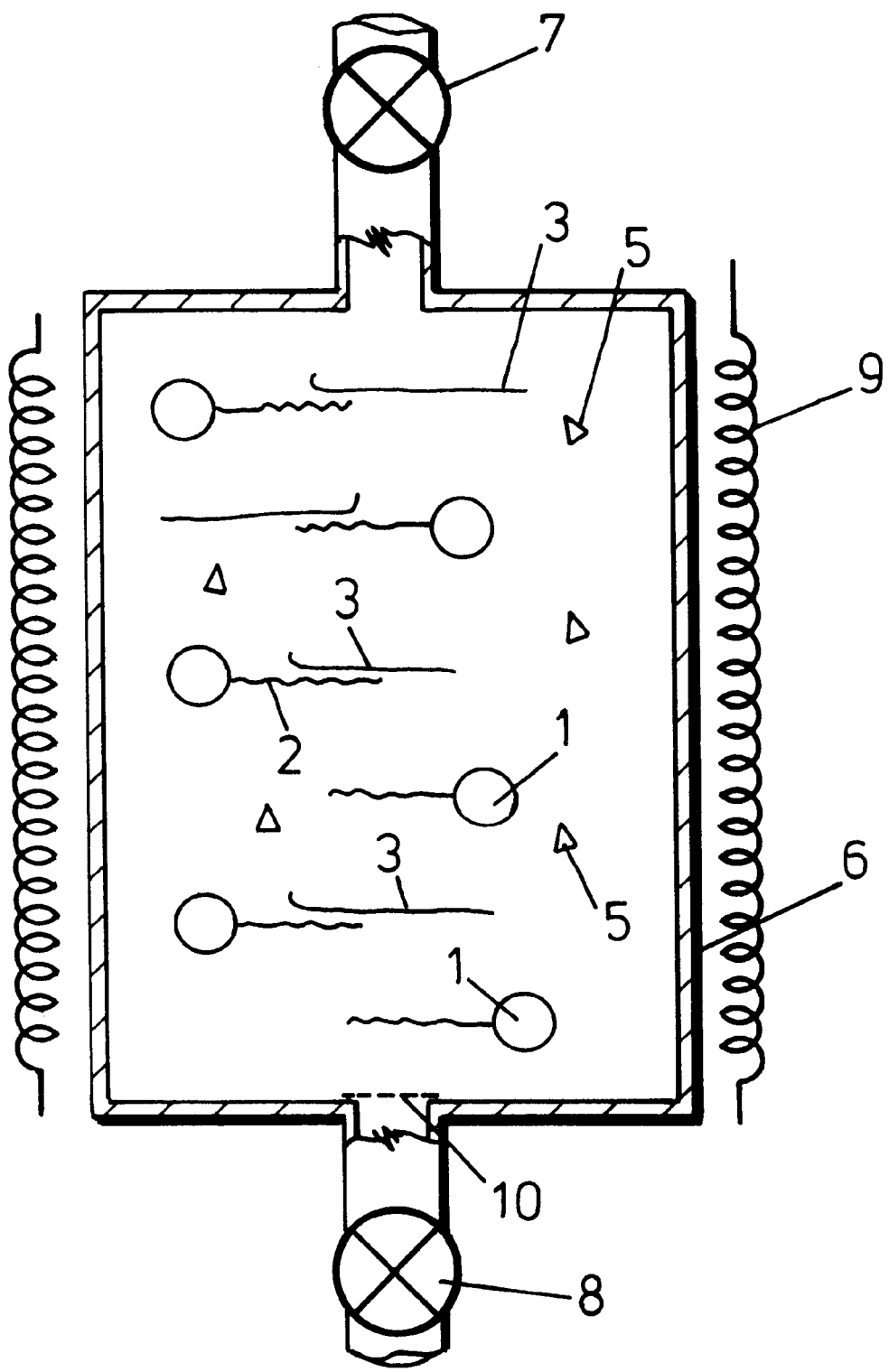
FIG. 2 shows a longitudinal section of a flow through column containing the oligo-solid system.

It is particularly preferred that the particles 1 are contained within a flow through column 6 (see FIG. 2) having inlet and outlet valves 7 and 8 as shown as well as a heater 9. The particles may be retained within the column by porous elements 10. For convenience, the particles 1 depicted in FIG. 2 are shown as having only one oligonucleotide sequence immobilised thereon.

The target nucleic acid is added to the flow through column via inlet valve 7 in a ratio of for example 1000:1 oligonucleotide:target in suitable buffer, e.g. high salt hybridisation buffer and hybridisation effected under conditions specific for the support bound oligonucleotide and target nucleic acid. When double stranded DNA is the source of the target nucleic acid, it is first separated into single strands by conventional methods either before being added to the column or whilst it is on the column.

Sample 4 is retained in the column by virtue of the outlet valve 8 being closed. After the hybridisation step, the unwanted impurities 5 (which are not immobilised on the support) may be removed by washing (with valve 8 open) to leave the clean sample target nucleic acid on the support.

Figure 3:
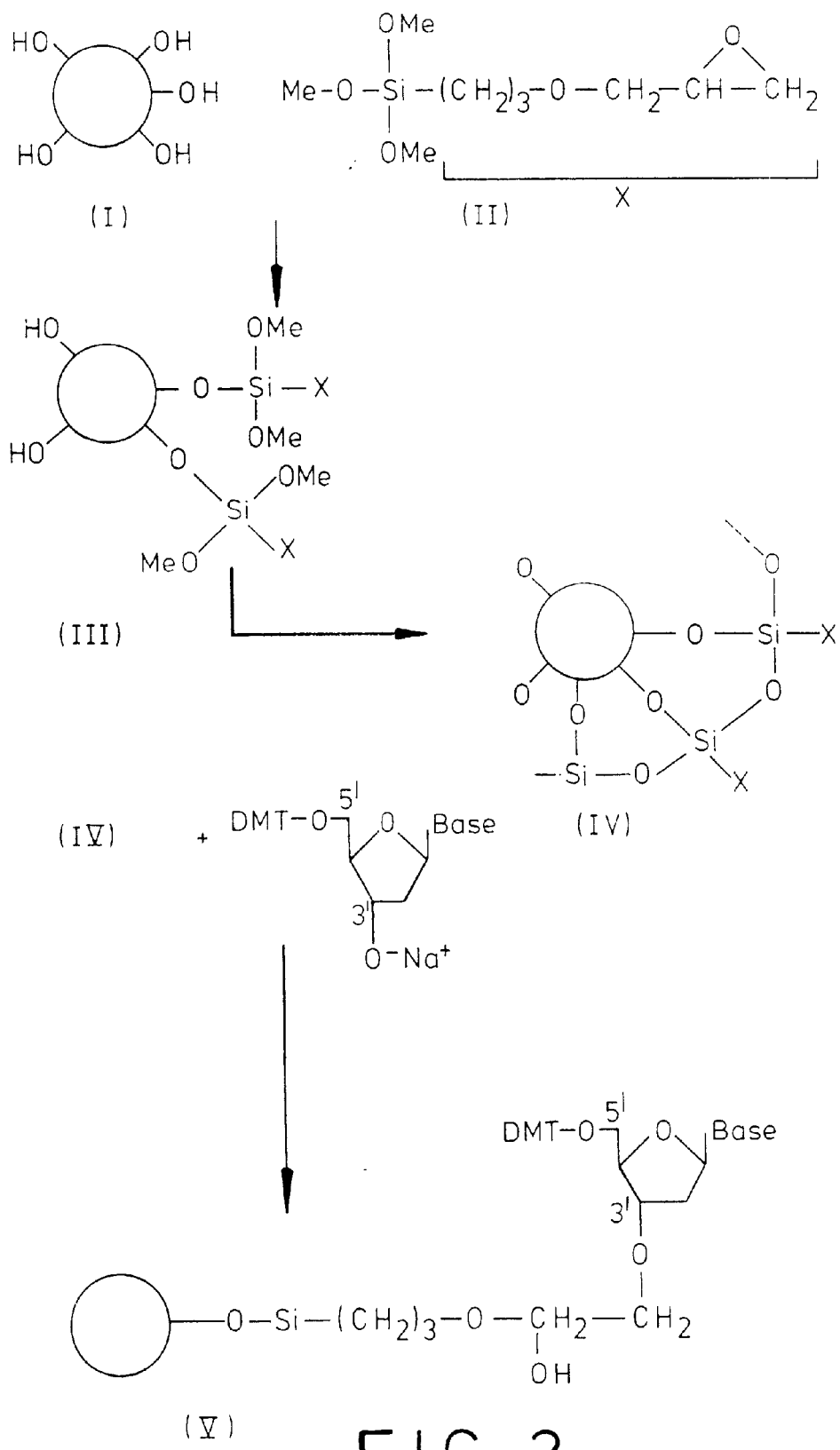
FIG. 3 illustrates a reaction path for obtaining a solid support for immobilising an oligonucleotide.
Figure 4B:
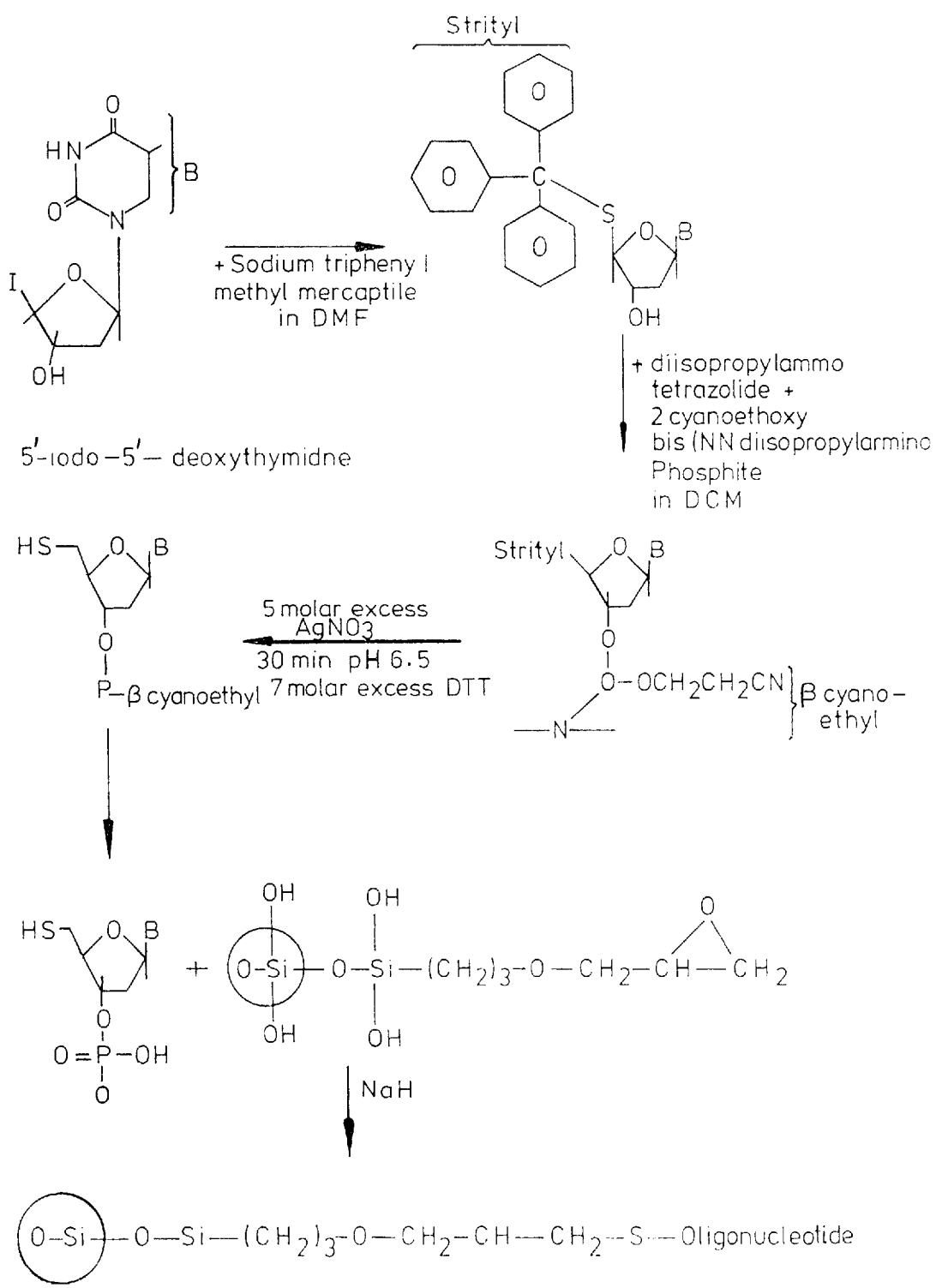

The manner in which the solid support (with immobilised oligonucleotide) is prepared is depicted in FIGS. 3–5. Reference is firstly made to FIG. 3 which illustrates one embodiment of reaction path for obtaining a support with reactive groups to which an oligonucleotide may be immobilised.

The procedure starts with silica gel particles (1) having surface hydroxyl groups as shown. In the first reaction step, the particles are treated with 3-glycidoxypropyl trimethoxy silane (II) e.g. at a temperature not in excess of 95° C. for 2 hours under a nitrogen atmosphere. As a result, a condensation reaction occurs whereby residues of (II) become bonded to the silica particle (I) to yield the product depicted as (III). Although the drawing shows only two residues bonded to the silica particle this is simply for the purpose of clarity and in practice considerably more of the residues will be bonded to the silica particle. Typically, the level of binding will be about 40–45 micromoles of (I)/gram of silica.

Product (III) is then washed in sequence with dry toluene, dry methanol, and dry ether.

The next step involves heating of the product to effect a cross-linking of the residues. Typically this cross-linking reaction is effected at a temperature of 110° C. for at least 2 hours. The resultant product is as shown at (IV) from which it will be seen that the silicon atoms are linked together through oxygen atoms.

Free hydroxyl groups remaining on the surface of the silica particle may if desired be capped with a chlorosilane. The capping agent may, for example be trimethyl chlorosilane with the reaction being conducted in pyridine for two hours at room temperature. Subsequent to capping, the support may be subjected to the above described washing operation.

The support thus obtained has free epoxy groups which may be used from immobilisation of an oligonucleotide.

It is possible for example using known procedures to synthesise an oligonucleotide in situ on the support, the oligonucleotide being complementary to a specific sequence on a target nucleic acid. Thus, the sodium salt of a dimethoxy trityl (DMT) protected nucleotide may be reacted with the support whereby the —O' moiety at the 3' position of the nucleotide reacts with the free epoxy group to yield product (V). The sodium salt may be prepared from the DMT nucleotide (which has been dried over $P_2O_5$) by dissolving in dry DMF, maintaining the solution under an anhydrous atmosphere, and adding sodium hydride. Subsequently the sodium hydride is filtered off to leave the sodium salt.

After removal of the DMT protecting group, a desired oligonucleotide to be synthesised from the individual nucleotides using known procedures for oligonucleotide synthesis.

Alternatively it is possible for a pre-synthesised oligonucleotide (complementary to a specific sequence on a target nucleic acid and preferably also containing a restriction endonuclease site) to be bound to the support.

A number of synthetic oligonucleotides are available complementary to a number of target nucleic acid sequences which may be used as probes to test for the presence of certain bacteria, viruses, parasites and the like, see appendix A. By way of specific example, the invention may be used, for example, for detecting the following, for which the oligonucleotide sequences given below would be immobilised on the support.

Where the oligonucleotide has protecting groups due to the synthesis reaction, such as butyl/isopropyl groups on the bases (G,A,C) of the 3'-5' oligos and β cyanoethyl groups of the 5'-3' oligos, these must be removed after synthesis. The oligo-solid support may be heated to 55° C. for 2 hours in 38% $NH_4OH$ to eliminate the protecting groups to give the deprotected oligonucleotide.

An example of a manipulation suitable for this system is amplification of the target nucleic acid sequence.

Figure 5A:
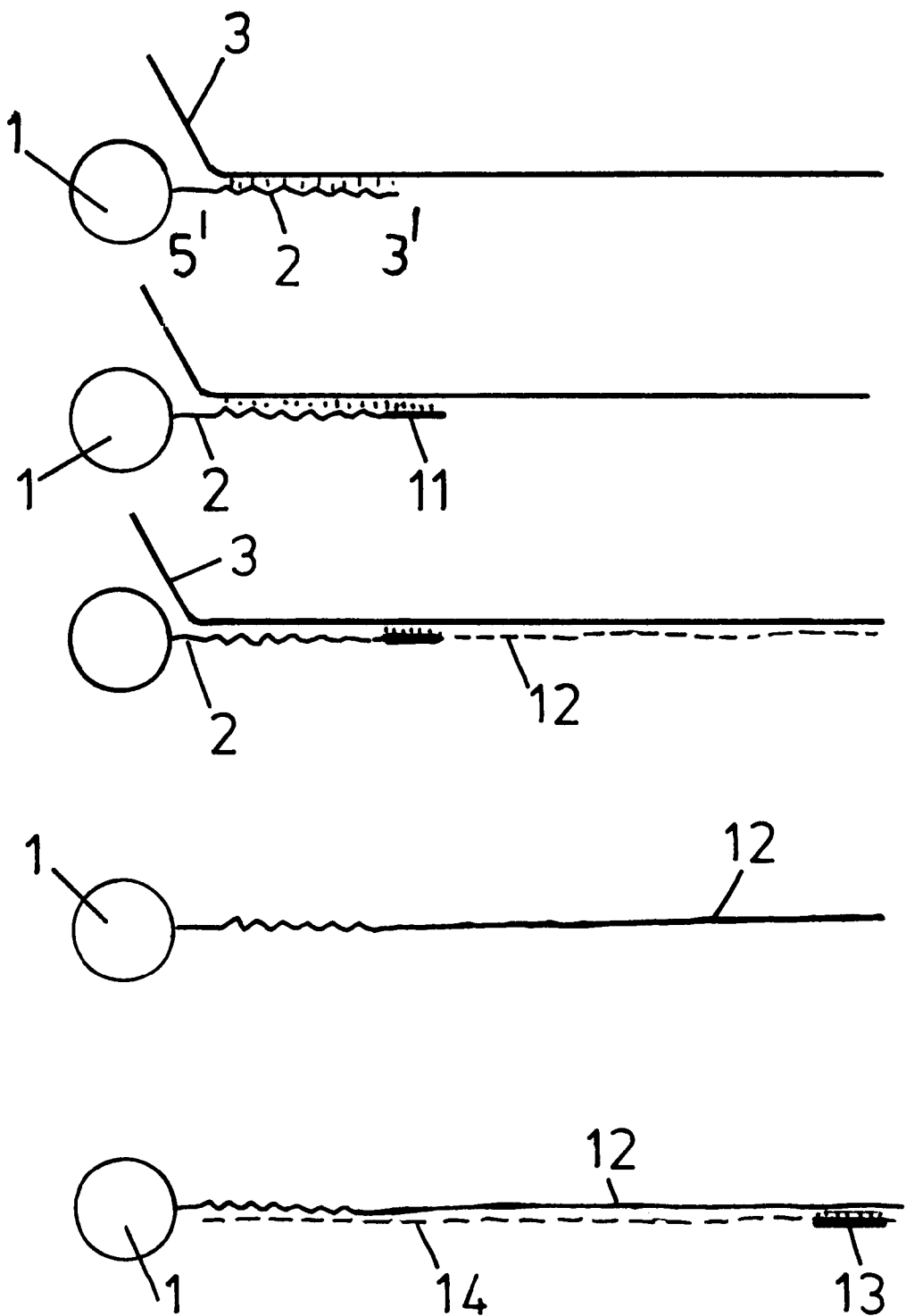
Figure 5B:
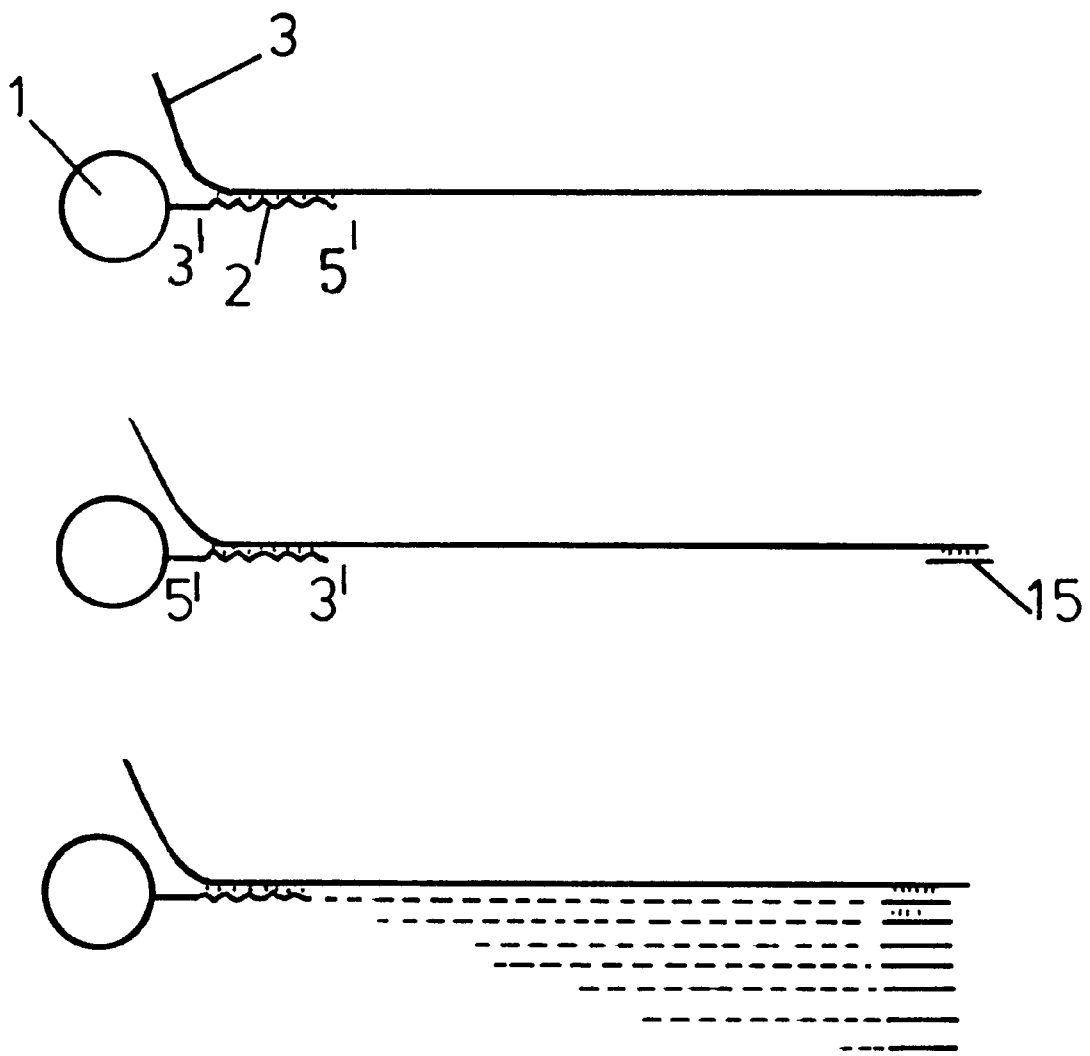
Figure 5C:
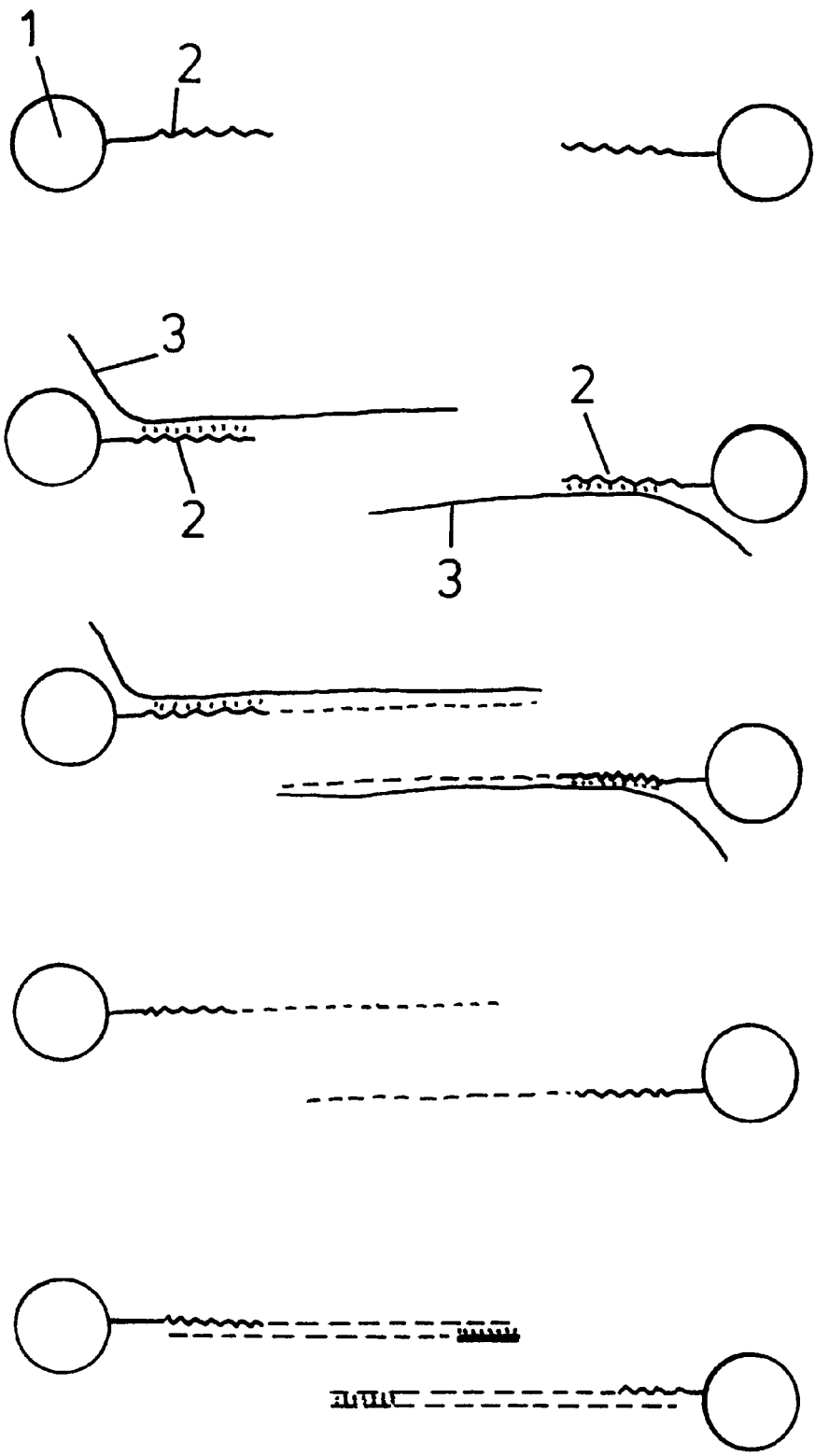

FIGS. 5a–c shows diagrammatically the steps involved in amplification techniques depending on the position of the primer site, orientation of the oligonucleotide (i.e. 3'-5' or 5'-3'), and therefore target nucleic acid sequence, and presence of one or two oligonucleotide sequences (i.e. reverse orientation oligos). The steps involved in amplification are known, i.e. addition of primer, primer extension, addition of a second primer to back copy the target copy, etc.

In the embodiment illustrated in FIG. 5a, the 5' end of the oligonucleotide may be bound to the support and the manipulation may be amplification of the target nucleic acid which is hybridised to the oligonucleotide. In this case, the oligonucleotide may serve as the primer or a separate primer 11 may be ligated to the oligonucleotide prior to the hybridisation step. In either case a primer extension product 12 is synthesised (using the target nucleic acid as a template) from the primer to the end of the target nucleic acid. There is thus obtained a nucleic acid sequence which is bound to the support and which is complementary to the target nucleic acid. For convenience, the complementary sequence is referred to herein as the "copy target".

The support may then be washed and the hybridised nucleic acid strands (i.e. the target and copy target) may

| Epsilon Bar Virus | 5'GACAACTCGG CCGTGATGGA-3' | (SEQ ID NO: 1) |
| Toxoplasma Gondii | 5'GGAACTGCAT CCGGTCATGA G-3' | (SEQ ID NO: 2) |
| Trypanosoma Brucei Brucei | 5'CGAATGAATA TTAAACAATG CG—CAG-3' | (SEQ ID NO: 3) |

The oligonucleotide may be bound to the support in either the 3'-5' or 5'-3' orientation. Binding in the 3'-5' orientation may be achieved by reacting the epoxy group on the support with a primary hydroxyl group of the sodium salt of a nucleotide (e.g. thymidine nucleotide (dimethoxytrityl deoxyribonucleoside (dT) (see FIG. 4a)) to produce a bond which is both acid and alkali stable, unlike currently used linkage groups.

Binding in the 5'-3' orientation may be achieved as follows (see also FIG. 4b) 5'-iodo 5'-deoxythymidine is reacted with sodium triphenyl methylmercaptile in DMF to form an S-trityl compound. This compound is further reacted with diisopropylammo tetrazolide and 2- cyanoethoxy bis(NN diisopropylamino) phosphoamidite in DCM to produce the β cyanoethyl. The S-trityl group is removed by reducing reactions by methods known in the art (Connolly, Nucleic Acid Research, 13, 12, 1985; Chu, Nucleic Acid Research, 16, 9, 1988; Guar, Nucleic Acid Research, 17, 11, 1989) before linking with the epoxy substituted support using sodium hydride. Other methods of preparing oligonucleotides for linkage in the 5'-3' orientation are known (Anisorge, Nucleic Acid Research, 15, 11, 1987; Sproat, Nucleic Acid Research, 15, 12, 1987; Zuckerman, Nucleic Acid Research, 13, 5305. 1987; Verheyden, JOREGA CHEM, 35, 2319, 1970), although this list is not exhaustive and any other method apparent to those skilled in the art may be used to prepare oligonucleotides in either the 3'-5' orientation of 5'-3' orientation for linkage to the solid support system of the present invention.

subsequently be denatured using techniques well known in the art (e.g. by heating at a particular temperature) to leave only the copy target bound to the solid support (via the oligonucleotide). For convenience, the solid support with bound oligonucleotide is also referred to in the subsequent description as the—"oligo-solid support".

The support system may be washed and the copy target which remains thereon may then be used for synthesising further quantities of the original target nucleic acid. Such synthesis will comprise hybridising a primer 13 to the copy target, washing the support to remove unhybridised primer, effecting primer extension (whereby the copy target serves as a template), and then denaturing and collecting the synthesised nucleic acid sequence 14. This process may be repeated as many times as necessary whereby the original target nucleic acid is, in effect, amplified to a desired degree. It will be appreciated that each amplification step uses the same set of copy target molecules.

The procedure illustrated in FIG. 5a is particularly suitable for detecting the presence of low quantities of a target nucleic acid in a medical sample. The primer 13 may be labelled by known techniques and a detection operation is performed to detect the correspondingly labelled nucleic acid sequence 14. If the label is detected then this is confirmation that the target nucleic acid 3 was present in the original sample.

As a modification of the procedure described for FIG. 5a, the double stranded nucleic acid may include a restriction site (e.g. as provided by a primer ligated to the oligonucleotide) and the appropriate restriction enzyme then used to cleave the double stranded molecule from the support.

In an alternative embodiment of the invention (see FIG. 5b), in which the 3' end of the oligonucleotide is bound to the support, the manipulation may involve sequencing of the hybridised target nucleic acid using standard methodology (e.g. Sanger DNA sequencing technique). Thus, a primer 15 may be hybridised to the target nucleic acid (which is hybridised to the oligonucleotide on the support). The primer must be one which will hybridise to the target at a temperature at which the latter does not melt off the oligonucleotide. A strand synthesis reaction is then effected with a mixture of the 4 deoxynucleotides (dATP, dTTP, dGTP) together with a single dideoxynucleotide. The synthesis proceeds in the 5'-3' direction from the primer towards the oligonucleotide. The reaction is carried out four times, using a different dideoxynucleotide each time. As is well known, the presence of the dideoxynucleotide causes nucleic acid sequences of different lengths to be obtained—as represented by the dashed lines. The products of the four reactions are run in parallel on an appropriate gel and the sequence determined from the positions of the bands in the four tracks. This particular embodiment of the invention is particularly suitable for detecting point mutations in a nucleic acid (provided, for example, as a medical sample) by comparing the sequence obtained with that of a control sample known to have the "normal" sequence.

The embodiment in which the 3' end of the oligonucleotide is bound to the support may also be used to amplify the target nucleic acid sequence. As in the case of sequencing described above, a primer may be hybridised to the target nucleic acid. The primer used must be one which hybridises to the acid at a temperature below that at which the target melts off the oligonucleotide. The extension of the primer is then effected under known conditions, the extension being effected towards, and as far as, the oligonucleotide. The copy product thus obtained may be melted off the target nucleic acid under conditions which leave the latter hybridised to the support for use in further amplification reactions.

In all of the amplification reactions described above, the same template remains bound to the oligo solid support and is used for further amplification reactions. This is a significant difference of the present invention over the technique disclosed in EP-A-0 200 362 since, in the latter, both strands of the target nucleic acid are used as templates and, once copied, the target strands and the copied strands are all used as templates for the second and further amplification steps. Thus should a mistake in the copying occur at any stage, the mistake is copied into the "chain reaction".

The present invention avoids this problem by either having a single copying stage and maintaining this copy of all future amplifications, or by maintaining the original target sequence for all amplifications. The present invention is also more efficient than that described in EP-A-0 200 362 since in the former non-hybridised primers and target or copy sequences are removed from the system by washing whereas, in the latter, unhybridised target, primer, and copy product are present in the method thus making the system inefficient.

In a still further embodiment (see FIG. 5c), two primers may be added which are complementary to different portions of the target or copy target, in either the 5'-3' or 3'-5' orientations, and which may be used to check the sequence for point mutations in a manner known in the art (DNA ligase annealing reaction). In this analysis, the primers are usually labelled and the test used for rapid diagnosis of, for example, P53 tumour suppressor gene mutations since 75% of all colon cancer patients have a point deletion in this gene.

It will be appreciated from the above description that the present process differs from known processes in that the solid phase system and apparatus of the present invention allow greater efficiency and yield of the amplified nucleic acid. This is due to the ability of the process to be carried out in steps. The column may be washed after each hybridisation to eliminate unhybridised DNA etc and "clean up" the system, greatly improving efficiency. The contents of the reaction solution on the column, i.e. newly amplified target sequence, may be diverted directly into a detector such as an optical cell connected to the column and the presence or absence of a target sequence confirmed quickly. This is particularly applicable to diagnosis of patient samples to test for the presence of any disease causing organism in a simple, quick and reliable manner not hitherto available.

Figure 5D:
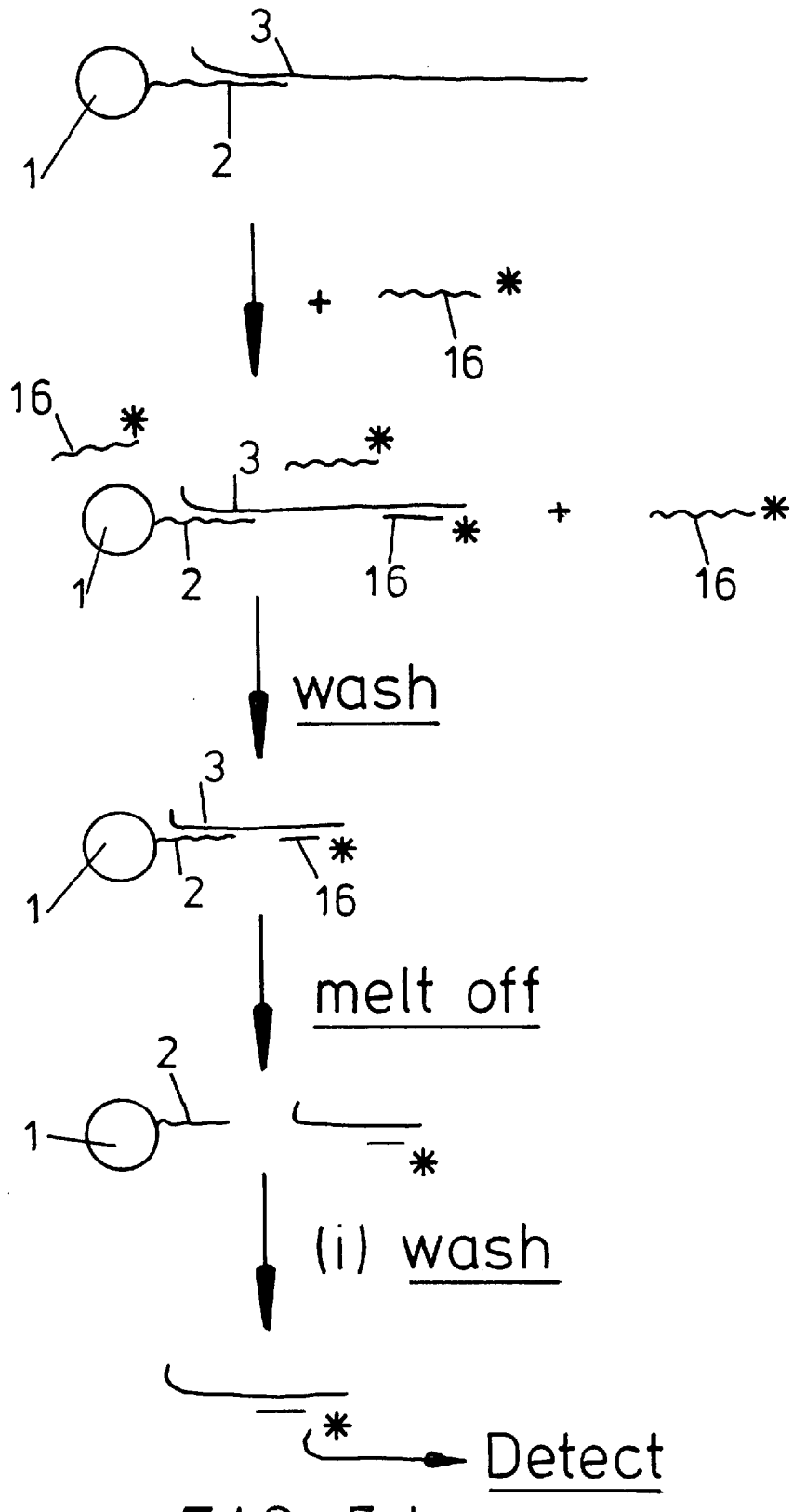

A further embodiment of the invention (which does not involve amplification) is illustrated in FIG. 5d which is applicable to the testing of samples for the presence (or otherwise) of a relatively large amount of a target nucleic acid. In the embodiment of FIG. 5d, a labelled primer 16 may be added to the support system, the primer being one which will hybridise to the target nucleic acid at a temperature below that at which the target melts off the oligonucleotide. If target nucleic acid 3 is present, the primer will hybridise thereto. The support may now be washed at a temperature below that at which the primer 16 melts off the target nucleic acid to remove unannealed primer 16. In the next stage, the solid support is heated to a temperature at which either primer 16 is melted off (either with or without target acid), the support is washed, and eluted product passed to a detector. If the label is detected then this demonstrates that presence of the target nucleic acid in the original sample.

Referring now to FIG. 6, there is illustrated an apparatus in which the hybridisation of the target nucleic acid to the support bound oligonucleotide as well as amplification reacts may be effected.

The apparatus illustrated in FIG. 6 comprises a column 20 (equivalent to column 6 of FIG. 2) pre-loaded with support particles 21 having oligonucleotide 22 bound thereto. Column 20 will typically have a volume of about 200 $\mu$l and has an inlet 23 and an outlet 24 provided with porous retaining elements 25 to maintain the particles 21 within the column. The apparatus has an arrangement of valves 26–34 as shown and also provided with a source of pressurised gas which may be applied in accordance with arrows G. The gas is used for effecting movement of reagents and products within the apparatus. Certain of the valves are arranged to provide venting of the gas as depicted by arrows V.

Valve 26 allows selective communication of the interior of column 20 with a reagent supply assembly 35 having individual vessels 35a–35d containing solutions (e.g. samples, primers, buffers etc) which are supplied to the column 20 via open valves 26 and 27, by means of gas pressure. Valve 29 may be used during this procedure to vent excess gas pressure.

On the outlet side of valve 28 is a transfer region 36 which may selectively communicate (via valve 30) with a product collection region 37 associated with a detector 38, which may, for example, be an optical detector, or a detector for a radiolabel. Other types of detectors may also be used.

Transfer region 36 may also selectively communicate (via valve 31) with a solution holding region 39 or a waste receptacle 40. The solution collection region 39 is provided by one of the tubular lines of the apparatus and has a volume at least equal to that of column 20.

A heater 41 is provided around the column as shown.

The valves of the illustrated apparatus may for example be zero dead Teflon seated valves (e.g. as available from General Valve (U.S.A) the tubing used in the apparatus may be 1.5 mm diameter Teflon tubing.

In use of the apparatus, the sample together with appropriate buffers is supplied to column 20 by gas pressure as previously indicated. Hybridisation of target nucleic acid is effected at the appropriate temperature and subsequently the column is washed (with solution supplied from assembly 35). The washings may be passed to waste receptacle 40 (via appropriately set valves 28 and 31). Valve 34 may be open during this procedure to vent excess pressure.

A manipulation may now be carried out on the target nucleic acid held on the support. For this purpose reagent solutions as appropriate as supplied from assembly 35 via appropriately set valves (both for liquid supply and for venting).

After the manipulation, the reagent solution may be passed from column 20 to solution holding region 39.

Manipulation product may now be melted off the support 21 and passed to product collection region 37 either for immediate detection or for storage.

If a further manipulation is to be effected on target nucleic acid (or copy thereof) on the support then the solution held in region 39 may be returned to column 20 under gas pressure through valve 32. The above process may then be repeated.

Manipulation product may be collected as often as required in region 37. During collection of product, valve 33 will be set to vent To prevent product being passed immediately to the detector, valve 33 may be closed after a short time so that collected product cannot pass sufficiently far along region 37 to reach detector 38. The provision of the gas supply to detector 38 allows a means of cleaning the detector when required.

It will be appreciated that the above described apparatus may be automated with the setting of the valves under electronic control.

The apparatus may comprise a single column as illustrated in FIG. 6 or may comprise a plurality of columns for testing a plurality of oligonucleotide probes on a single sample, or for testing a single oligonucleotide probe (e.g HIV I) on a plurality of samples.

Additionally, column 20 need not be a fixed part of the apparatus. It is possible for example, to provide disposable columns 20 pre-loaded with solid support having oligonucleotide bound thereto, and then to locate the column in an apparatus otherwise as shown in FIG. 6. This avoids the need, which would be required for a fixed column, of emptying solid support from column.

The invention will be described by the following non-limiting Examples. The oligonucleotides used in the Examples—both column bound and column cleaved (primer samples) were synthesised by a standard coupling programe on a Biosearch Model 8500 DNA synthesizer. β-cyanoethyl protected phosphoamidites were utilised for the synthesis. The column cleaved primer samples were fully deblocked (all DMTr groups removed) and were automatically $NH_4OH$ cleaved from the CPG columns. The column bound oligonucleotides were not $NH_4OH$ cleaved and the final DMTr group was not removed unless stated. Following synthesis both column bound and column cleaved oligonucleotides were transferred to screw topped tubes with 38% $NH_4OH$ (1 ml). The tubes were placed, in clamps, for 1 hour in a 55° C. oven, to remove protecting groups. The tubes and clamps were then transferred to a −20° C. freezer for 10 minutes. The $NH_4OH$ supernatant was removed from the column bound oligonucleotides and discarded. The samples were freeze dried in a Savant centrifugal drier and stored in a desiccator. Each column cleaved oligonucleotide was divided into three tubes and freeze dried. One of these tubes was then taken and the crude oligonucleotide present purified.

EXAMPLE 1

Preparation of Silica Gel Support

Calcined Spherisorb GC support (1 g) was taken and dried over $P_2O_5$ round bottomed flask with 40 ml of anhydrous toluene. The contents of the flask were stirred with a magnetic stirrer and the resulting slurry heated to 90–95° C. in an oil bath. Anhydrous 3-glycidoxypropyl trimethoxy silane (1.5 ml) was added to the slurry and the reaction allowed to proceed, with stirring, for three hours at 90–95° C. Care was taken to ensure that the temperature did not exceed 95° C. After three hours the reaction mixture was cooled to room temperature, filtered, and washed with anhydrous toluene (40 ml), methanol (40 ml), and ether (20 ml). The functionalized silica gel was dried over $P_2O_5$ and silica overnight.

EXAMPLE 2

Synthesis of Cytosine Nucleotide Substituted Support (a) Preparation of the sodium salt of the C nucleotide derivative: Dimethoxytrityl deoxyribonucleoside cytosine (DMTr dC) (1 g) was taken and dried over $P_2O_5$ and silica for several days. The dried DMTr dC was dissolved in anhydrous N, N-dimethylformamide (DMF) (20 ml) under nitrogen. After solution was complete, sodium hydride (0.6 g) was added and allowed to react with the DMTr dC in anhydrous AMF for 20 minutes with stirring. The NaH was then filtered off from the reaction mixture.

(b) Reaction of the prepared silica gel and nucleoside derivative: The dried silica gel support was added directly to the filtered sodium slat of the nucleoside and the mixture stirred, under reflux, for two hours. The coupled nucleoside and support mixture was cooled to room temperature overnight. The substituted silica support was filtered through a silonised sintered glass filter and washed with 20 ml each of anhydrous DMF, anhydrous toluene, methanol, methanol and ether. Finally, the solid support was dried and stored in a desiccator.

The 5' oxygen of the sugar portion of the nucleoside derivative is protected by a DMTr group, this is acid labile and can be removed by anhydrous acids such as dichloroacetic acid (DCA), generating a bright orange DMTr cation. A portion of the dried substituted support was treated with dichloroacetic acid (1 ml of 2% DCA in dichloromethane) and a bright orange colour was seen, indicating that the coupling of the support silica and cytosine nucleoside derivative had been successful.

EXAMPLE 3

As a test system a procedure was set up to isolate a clone from a mixture of bacterial and viral DNA. The target sequence (cloned gene) was located within the bacteriophage M13 mp and contained the following two sequences

5'GCGGGTCCCA AAAGGGTCAG TGCTG-3'   (SEQ ID NO:4)

5'AGTGTGTCCT TTGTCGATAC TG-3'   (SEQ ID NO:5)

M13 mp is a standard virus used in molecular biology and is used routinely as a sequencing vehicle.

An oligonucleotide of the following sequence, i.e. homologous to sequence SEQ ID NO:4, was synthesised onto the support produced in Example 2.

5'CGCCCAGGGT TTCCCAGTCA CGAC-3'   (SEQ ID NO:6)

The cytosine residue at the left hand end of the above sequence is that which was incorporated in the support produced in Example 2.

The solid support (15 mg) with oligonucleotide sequence bound thereto was then placed in a flow through column and a mixture of E. coli (product of $10^8$ cells) and 1 μg of M13 DNA was placed onto the column after being denatured by heat. The column was maintained at a temperature of $(T_m-2)°C$. where Tm is the melting temperature of sequence SEQ ID NO:6 as calculated by the formula $$T_m=2(A+T)+3(G+C)$$

where A, T, G and C are respectively the number of Adenine, Thymine, Guanine and Cytosine residues in sequence SEQ ID NO: 6.

Since the column is maintained slightly below the melting temperature $(T_m)$ the viral DNA is able to anneal to the bound oligonucleotide.

The column was maintained at $(T_m-2)°C$. and washed with 2½ milliliters of annealing buffer (10 mM $MgCl_2$ and 10 mM TRIS HCl pH 7.5). The washings from the column were collected in 200 μl fractions (11 in total in tubes.

Each of the collected fractions was then subject to a standard sequencing reaction (Sanger Coulson method) by addition of 1 ng of sequence SEQ ID NO: 6 above to each of the tubes together with DNA polymerase (Klenow fragment) and deoxyribonucleotides and dideoxyribonucleotides in the standard reaction mixture. $^{32}P$ labelled deoxythymidine was also added to the reaction mixture.

A sequence reaction was also performed on the material immobilised on the column. The column bound material was melted off the column and collected. Sequencing was performed using the same reaction mixture as that employed in the solution phase sequencing.

The products of the sequence reactions, both support bound and solution phase, were then developed on a standard 8% polyacrylamide gel using standard procedures. The results are shown in the autoradiograph of FIG. 7 in which

| Lane | Explanation |
| --- | --- |
| 1 | Sequence produced on solid support bound material after washing with 2.5 ml of annealing mix |
| 2 | First 200 μl sequence produced |
| 3 | Second 200 μl sequence produced |
| 4 | Etc |
| 5 | " |
| 6 | " |
| 7 | " |
| 8 | " |
| 9 | " |

-continued

| Lane | Explanation |
| --- | --- |
| 10 | " |
| 11 | " |
| 12 | " |

Lane 1 demonstrates that the target nucleic acid (viral DNA) was indeed bound to the support (as proven by the fact that the primer sequence SEQ ID NO: 6 was able to anneal to the target nucleic acid and permit the sequencing reaction to take place). Lanes 1–10 also demonstrate that there is no cross-talk or smear from the E. coli DNA. Therefore the viral DNA had been selectively retained on the support. Additionally the support bound target DNA is stably held on the support. There is no steric hindrance of the Klenow fragment by the support itself since sequencing reactions have been performed on support bound DNA.

Lanes 2–12 demonstrate progressively decreasing amounts of target DNA (i.e. viral DNA) in the washings from the column. Therefore excess viral DNA had been added to the column and was not annealed to the oligonucleotide sequence SEQ ID NO: 6. It is therefore possible to "tune" the binding capacity of the column to the concentration of target nucleic acid.

APPENDIX A

Animal viruses

Pig Parvovirus
Pigmycoplasma hypneumoniae
Herpes

Cytomegalovirus (CMV)
Epstein Barr
Simplex Herpesvirus
Papillomaviruses

Human Papilloma virus 6 (HPV)
Human Papilloma virus 11
Human Papilloma virus 16
Human Papilloma virus 18
Human Papilloma virus 33
Parvoviruses Parvovirus B 19
Picornaviruses Rhinovirus (Enterovirus)
Rhinovirus HRV 2-14
Hepatitus virus Hepatitis A (HPV)
Hepatitis B
Hepatitis C
Hepatitis D
Retroviruses Human immunodeficiency virus 1 (HIV I)
Human immunodeficiency virus 2 (HIV II)
Human T cell lymphoblastic virus I (HTLV I)
Human T cell lymphoblastic virus II (HTLV II)
Bacteria Legionella pneumophilia
Mycobacterium avium
bovis
fortuitum
tuberculosis
Mycoplasma pneumoniae
Escherichia coli toxin
Borrelia burgdorferi
Clamydia trachomatis
Salmonella Typhimurium

APPENDIX A-continued

Staphylococcus Aureus
Clostridium Perfringens
Klebsiella Pneumoniae
Aeromonas Salmonicida
Mycobalterium Bovis
Parasites Trypanosoma:

*Trypanosoma brucel brucei*
*Trypanosoma cruzi*
*Trypanosoma congolense*
Toxoplasma

*Toxoplasma gondii*
Plasmodia

*Plasmondium falciparum*
*ovale*
*vivax*
*malariae*

SUMMARY OF SEQUENCES

SEQ ID NO:1 is the nucleotide sequence of a probe which hybridizes with a corresponding region of the nucleotide sequence of Epsilon Bar Virus.

SEQ ID NO:2 is the nucleotide sequence of a probe which hybridizes with a corresponding region of the nucleotide sequence of Toxoplasma Gondii.

SEQ ID NO:3 is the nucleotide sequence of a probe which hybridizes with a corresponding region of the nucleotide sequence of Trypanosoma Brucei Brucei.

SEQ ID NO:4 is the nucleotide sequence located within the bacteriophage M13 mp.

SEQ ID NO:5 is the nucleotide sequence located within the bacteriophage M13 mp.

SEQ ID NO:6 is the nucleotide sequence of a probe which is homologous to sequence ID NO:4 of the bacteriophage M13 mp.

I claim:

1. Apparatus for effecting a manipulation on a nucleic acid sequence comprising a flow through vessel containing a solid support system to which is bonded single stranded oligonucleotide complementary to a specific sequence on a target nucleic acid, storage means for storing solutions removed from the vessel during washing or other procedures, before the solutions are returned to the column, detector means for detecting products of nucleic acid manipulations, and control means for diverting solutions into and out of the vessel, into waste or storage areas and to the detector means, wherein the solid support system comprises a particulate solid support system having a cross-linked siloxane matrix in which silicon atoms are bonded to the support and are cross-linked together by —O— linkages and to which is bonded the single stranded oligonucleotide.

2. A method of effecting a manipulation of a nucleic acid sequence, comprising the steps of:

(a) providing in a flow-through vessel a solid support system having covalently bonded thereto, single stranded oligonucleotides having a sequence of bases complementary to a portion of the sequence of a particular target nucleic acid having a greater number of bases than the oligonucleotide, the oligonucleotides being specific for the target nucleic acid, (b) adding a source of single stranded target nucleic acid to the solid support system, (c) hybridizing the target nucleic acid to the oligonucleotides, (d) effecting a flow through washing of the support after the hybridization to remove any non-hybridized target nucleic acid in the support system thereby providing a pure sample of the target nucleic acid on the solid support system, and (e) effecting on the target nucleic acid immobilized on the support in the flow through vessel a manipulation selected from the group consisting of copying of, denaturation of and/or hybridization to the target nucleic acid.

3. The method of claim 2 wherein the flow through vessel comprises a column.

4. The method of claim 2 wherein the solid system comprises silica.

5. The method of claim 2 wherein the solid support system comprises a plurality of particles.

6. The method of claim 5 wherein the plurality of particles comprises a plurality of non-porous particles.

7. The method of claim 5 wherein each of the plurality of particles has a size between and 100 microns and about 200 microns.

8. The method of claim 2 wherein the oligonucleotides are covalently bonded to the solid support system by base stable covalent bonds.

9. The method of claim 8 wherein the bonds are stable for not less than about 2 hours in an environment of about 38% $NH_4OH$ at a temperature of about 55° C.

10. The method of claim 2 wherein the solid support system comprises a cross-linked siloxane matrix in which silicon atoms are bonded to the support and are cross-linked together by —O— linkages.

11. The method of claim 2 wherein the flow through vessel has a column volume of between about 150 $\mu$l and about 250 $\mu$l.

12. The method of claim 2 wherein the manipulation comprises copying of the target nucleic acid sequence to produce a copy of at least a part of the sequence.

13. The method of claim 12 wherein the oligonucleotide has a 5' end and a 3' end, wherein the 5' end and the 3' end define a direction, wherein the 5' end of the oligonucleotide is covalently bonded to the support, and wherein the copying comprises extending the oligonucleotide in the 5' to 3' direction using the hybridized target nucleic acid as a template, thereby producing an immobilized copy of the target covalently bonded to the support.

14. The method of claim 13 further comprising the steps of:

(i) denaturing the target nucleic acid from the immobilized copy of the target nucleic acid covalently bonded to the support, (ii) effecting a flow through wash of the solid support system to remove the target nucleic acid therefrom, (iii) hybridizing a primer to the immobilized copy of the target nucleic acid covalently bonded to the support, and (iv) extending the primer in the 5' to 3' direction back towards the solid support using the copy of the target nucleic acid as a template thereby producing an extended primer product.

15. The method of claim 14 further comprising the steps of (v) denaturing the extended primer product from the immobilized copy, and (vi) collecting the extended primer product.

16. The method of claim 15 comprising repeating each of the steps (i)–(vi) at least once.

17. The method of claim 14 wherein the primer added in step (iii) is labeled so as to produce labeled extended primer product and the method further comprises the step of detecting the labeled extended primer product.

18. The method of claim 12 wherein the 3' end of the oligonucleotide is covalently bonded to the support, wherein the method comprises the step of hybridizing a primer to the target nucleic acid, and wherein the copying comprises extending the primer in the 5' to 3' direction back towards the support to produce an extended primer product.

19. The method of claim 18 further comprising the step of denaturing the extended primer product from the target nucleic acid while leaving the target nucleic acid hybridized to the oligonucleotide.

20. The method of claim 18 wherein the method comprises a sequencing reaction comprising the steps of:
  (i) effecting the copying reaction with a mixture comprising the four deoxynucleotides dATP, DTTP, dGTP and dCTP together with a first one of the four dideoxynucleotides, ddATP, ddTTP, ddGTP and ddCTP,
  (ii) denaturing and collecting the extended primer products while leaving the target nucleic acid hybridized to the oligonucleotide,
  (iii) repeating steps (i) and (ii) in turn with each of a second, third and fourth of the four dideoxynucleotides, and
  (iv) analyzing the collected extended primer products to determine the sequence of the target nucleic acid.

21. The method of claim 2 wherein the manipulation comprises denaturation of the target nucleic acid from the oligonucleotides.

22. The method of claim 2 wherein the manipulation comprises hybridization of a labeled probe to the target nucleic acid.

23. Apparatus for effecting a manipulation on a nucleic acid sequence, comprising:
  a flow through vessel provided with a solid support system to which are covalently bonded, by base stable linkages, single stranded oligonucleotides having a sequence of bases complementary to a portion of the sequence of a particular target nucleic acid having a greater number of bases than the oligonucleotide, the oligonucleotide being specific for the target nucleic acid,
  storage means for storing solutions removed from the vessel during washing to other procedures before the solutions are returned to the vessel,
  detector means for detecting products of nucleic acid manipulations, and
  control means for diverting solutions into and out of the vessel, into waste or storage areas and to the detector means.

24. The apparatus of claim 23 wherein the flow through vessel comprises a column.

25. The apparatus of claim 23 wherein the solid support system comprises a plurality of particles.

26. The apparatus of claim 25 wherein each of the plurality of particles has a size of between about 100 microns and about 200 microns.

27. The apparatus of claim 25 wherein the plurality of particles comprises a plurality of non-porous particles.

28. The apparatus of claim 25 wherein the plurality of particles comprise silica.

29. The apparatus of claim 23 wherein the oligonucleotides are covalently bonded to the solid support by covalent bonds which are stable for at least about 2 hours in an environment of about 38% $NH_4OH$ at a temperature of about 55° C.

30. The apparatus of claim 23 wherein the solid support system is provided with a cross-linked siloxane matrix in which silicon atoms are bonded to the support and are cross-linked together by —O— linkages and to which the oligonucleotides are covalently bonded to provide the acid and base stable linkage of the oligonucleotides to the solid support system.

31. The apparatus of claim 23 wherein the vessel has a volume of between about 150 µl and about 250 µl.

32. A flow through vessel having an inlet and an outlet and containing a solid support system having covalently bonded thereto, by base stable linkages, single stranded oligonucleotides having a sequence of bases complementary to a portion of the sequence of a particular target nucleic acid having a greater number of bases than the oligonucleotide, the oligonucleotide being specific for the target nucleic acid, the vessel having porous retaining elements to retain the plurality of particles in the vessel.

33. The vessel of claim 32 comprising a column.

34. The vessel of claim 32 wherein the solid support system comprises a plurality of particles.

35. The apparatus of claim 34 wherein each of the plurality of particles has a size of between about 100 microns and 200 microns.

36. The vessel of claim 34 wherein the plurality of particles comprise a plurality of non-porous particles.

37. The vessel of claim 34 wherein the plurality of particles comprise silica.

38. The vessel of claim 32 wherein the oligonucleotides are covalently bonded to the solid support system by covalent bonds which are stable for at least about 2 hours in an environment of about 38% $NH_4OH$ at a temperature of about 55° C.

39. The vessel of claim 32 wherein the plurality of particles are provided with a cross-linked siloxane matrix in which silicon atoms are bonded to the support and are cross-linked together by —O— linkages and to which the oligonucleotides are covalently bonded to provide the acid base stable linkage of the oligonucleotides to the plurality of particles.

40. The vessel of claim 33 wherein the vessel has a volume of between about 150 µl and about 250 µl.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA PROBE"

(ix) FEATURE:
       (A) NAME/KEY: misc_feature
       (B) LOCATION: 1..20

(xi) SEQUENCE DESCRIPTION: SEQ ID NO:1:

GACAACTCGG CCGTGATGGA                                                      20

(2) INFORMATION FOR SEQ ID NO:2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA probe"

(ix) FEATURE:
       (A) NAME/KEY: misc_feature
       (B) LOCATION: 1..21

(xi) SEQUENCE DESCRIPTION: SEQ ID NO:2:

GGAACTGCAT CCGTTCATGA G                                                    21

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA probe"

(ix) FEATURE:
        (A) NAME/KEY: misc_feature
        (B) LOCATION: 1..25

(xi) SEQUENCE DESCRIPTION: SEQ ID NO:3:

```
CGAATGAATA TTAAACAATG CGCAG                                    25
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: BACTERIOPHAGE M13

(ix) FEATURE:
        (A) NAME/KEY: misc_feature
        (B) LOCATION: 1..25

(xi) SEQUENCE DESCRIPTION: SEQ ID NO:4:

```
GCGGGTCCCA AAAGGGTCAG TGCTG                                    25
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: BACTERIOPHAGE M13

(ix) FEATURE:
        (A) NAME/KEY: misc_feature
        (B) LOCATION: complement (1..22)

(ix) FEATURE:
        (A) NAME/KEY: misc_feature
        (B) LOCATION: 1..22

(xi) SEQUENCE DESCRIPTION: SEQ ID NO:5:

```
AGTGTGTCCT TTGTCGATAC TG                                       22
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA PROBE"

```
(ix) FEATURE:
    (A) NAME/KEY: misc_feature
    (B) LOCATION: 1..24

(xi) SEQUENCE DESCRIPTION: SEQ ID NO:6:

CGCCCAGGGT TTCCCAGTCA CGAC                                              24
```